United States Patent [19]

Blum

[11] 4,017,530
[45] Apr. 12, 1977

[54] PHENOXY SUBSTITUTED THIOLCARBOXYLIC ACID AMINO ACID SUBSTITUTED ESTERS

[76] Inventor: Jean Blum, 20 Ter rue de Bezons, Appt. 2275, 92 400 Courbevoie, France

[22] Filed: Apr. 3, 1975

[21] Appl. No.: 564,633

Related U.S. Application Data

[63] Continuation-in-part of Ser. No. 465,306, April 29, 1974, abandoned.

[30] Foreign Application Priority Data

May 4, 1973 France .................. 73.16162

[52] U.S. Cl. ............... 260/455 R; 260/294.8 R; 424/301; 424/263
[51] Int. Cl.² ........................ C07C 153/07
[58] Field of Search ............... 260/455 R

[56] References Cited

UNITED STATES PATENTS

| 3,178,466 | 4/1965 | McDowell et al. | 260/455 R |
| 3,311,652 | 3/1967 | Richter et al. | 260/455 R |
| 3,333,945 | 8/1967 | Richter et al. | 260/455 R |
| 3,445,221 | 5/1969 | Regal | 260/455 R |

OTHER PUBLICATIONS

Bull. Soc. Chim., (1960) France, pp. 1786–1794.

Chem. Abst., vol. 63, (1965), 17948c.
Chem. Abst., vol. 49, p. 6231.
Chem. Abst., vol. 78, 119107r.
Chem. Abst., vol. 73, p. 97857c.

*Primary Examiner*—Lewis Gotts
*Assistant Examiner*—D. R. Phillips
*Attorney, Agent, or Firm*—Burgess Ryan and Wayne

[57] ABSTRACT

This invention concerns novel thiolesters of the formula

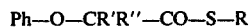

Ph—O—CR'R''—CO—S—R wherein
Ph is an aryl group which may be substituted;
R is an organic radical other than a phenol or a mercaptan group;
R' is hydrogen or a hydrocarbon radical, preferably an aliphatic group;
R'' is an aliphatic, cycloaliphatic, aromatic or heteroaromatic group, which is not aliphatic when R' is hydrogen.

The invention also concerns a new process for preparing the novel thiolesters.

3 Claims, No Drawings

PHENOXY SUBSTITUTED THIOLCARBOXYLIC ACID AMINO ACID SUBSTITUTED ESTERS

This application is a continuation-in-part of Ser. No. 465,306 filed Apr. 29, 1974 now abandoned.

This invention concerns a new process for manufacturing thiolesters of aryloxyacetic acid, substituted or unsubstituted, and also covers, as new industrial products, aryloxyacetic acid thiolesters which do not contain a mercaptan or free phenol group. It further relates to pharmacological applications of these new thiolesters.

This new process for manufacturing aryloxyacetic acid thiolesters differs fundamentally from existing processes, in that the process is conducted in an aqueous solution, by reaction between the selected aryloxyacetic acid halide and a metallic salt, generally an alkaline salt, of a mercaptan. The advantage of this aqueous phase process is that it is no longer necessary, as in existing processes, to use an organic solvent, which is usually expensive, and which raises regeneration and discharge problems. However, when water is used as a solvent, it is easy to separate the aqueous phase and the thiolester; the water can be purified cheaply, and easily regenerated. In addition, the alkaline reagent used in combination with water is a product easily obtainable on the market, such as NaOH or Ca(OH)$_2$, at low cost, whereas the basic additive used in the organic phases is quite costly.

This invention also concerns thiolesters obtained by this new process.

It also covers new thiolesters belonging to the series of aryloxyacetic thiolesters of the formula:

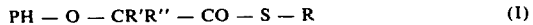

$$PH - O - CR'R'' - CO - S - R \qquad (I)$$

wherein
Ph is an aryl group such as phenyl which may be substituted such as a p-halophenyl group, i.e., p-chlorophenyl, p-iodophenyl, p-fluorophenyl, and the like;
R is an alkyl group containing up to and including 12 carbon atoms which may be substituted with a hydroxy, a p-halophenoxy isobutyryloxy, carboxy, lower alkoxycarbonyl, aryl, substituted aryl, acylamido, acylamidophenyl, pyridinyl, imino-aryl, substituted imino-aryl, i.e., with both carboxy and acetamido substituents or with both alkoxy carbonyl and acetamido substituents; an organic radical other than a phenol or a mercaptan group but which includes a phenyl and a tolyl radical, and the like; a substituted aryl group wherein the aryl group is a phenyl or tolyl group; an imino-aryl group wherein the aryl group is a phenyl group; an acyl group containing up to six carbon atoms such as acetyl, propionyl, butyryl, and the like;
R' is hydrogen or a hydrocarbon radical suitably an aliphatic group such as methyl, ethyl, propyl, butyl, isopropyl, isobutyl, hexyl, cyclohexyl, and the like;
R'' is an aliphatic group such as methyl, ethyl, butyl, hexyl, capryl, and the like; a cycloaliphatic group such as cyclopropyl, cyclobutyl, cyclohexyl, and the like; an aromatic group such as benzyl, phenyl, tolyl, etc., or a heteroaromatic group such as pyridine, morpholine, and the like, which is not an aliphatic group when R' is hydrogen.

In one embodiment of the invention, Ph is a p-chlorophenyl group.

In another embodiment of the invention, R' and R'' are methyl groups, or one is a hydrogen atom and the other a phenyl group, possibly substituted.

In one embodiment of the invention, Ph is a p-chlorophenyl group, R' and R'' are methyl groups, and R may be a group which, together with S, forms a group SR, which is any one of the following groups: (N-acetyl) cysteine, β-mercaptoethanol, p-chlorophenoxy-2-isobutyryl-O-mercaptoethanol, carboxymethylthio, (N-acetyl) homocysteine, and the like.

The invention also concerns processes for preparing new thiolesters of the formula (I) above, in which a substituted aryloxyacetic acid halide reacts with a mercaptan in an inert, neutral or basic organic medium, the mercaptan and possibly phenol group or groups contained in the mercaptans react with the substituted aryloxyacetic acid halide. The basic organic medium preferably consists of at least one of the substances belonging to the group comprising pyridine, triethylamine, trimethylamine, dimethylaniline, dimethylformamide and hexametapol.

This invention also relates to the pharmacological applications of thiolesters of the formula (I) above, to produce analgesic, hypocholesterolemient, hypolipemient and hepatoprotective effects, and more specifically applies to drugs for human or animal treatment, containing one or more thiolesters of the formula (I) above, as their active or secondary principle, possibly combined with a suitable carrier or vehicle. Drugs covered by this invention may be administered orally, rectally or parenterally, preferably in doses of approximately 200 mg to 1 g, twice or three times daily, depending on body weight. The compounds of this invention are administered orally, in adults, in doses ranging between 50 mg and 1 g in 3 or 4 daily doses, depending on body weight. The therapeutic compounds can be administered in any suitable carrier in the form of a pill, capsule, syrup, or other liquid forms, and the like.

The compounds of this invention are valuable in that they exert a lipid lowering effect. These compounds are comparable in activity to clofibrate but do not exhibit the toxicity of clofibrate with respect to liver.

Suitable aryloxyacetic thiolesters include, for example:
(N-acetyl) homocystein p-chlorophenoxy-isobutyrate of the formula pCl—C$_6$H$_4$—O—C(CH$_3$)$_2$—COS—(CH$_2$)$_2$—CH—(COOH)—NH—CO—CH$_3$ and its esters;
(N-acetyl) cysteine p-chlorophenoxy-isobutyrate of the formula pCl—C$_6$H$_4$—O—C(CH$_3$)$_2$—CO—S—CH$_2$—CH—(COOH)—NH—CO—CH$_3$ and its esters;
β-mercaptoethanol p-chlorophenoxy-isobutyrate of the formula pCl—C$_6$H$_4$—O—C(CH$_3$)$_2$—CO—S—CH$_2$—OH;
β-mercaptoethanol di-p-chlorophenoxy-isobutyrate of the formula pCl—C$_6$H$_4$—O—C(CH$_3$)$_2$—CO—S—CH$_2$—CH$_2$—O—CO—C—(CH$_3$)$_2$—O—C$_6$H$_4$pCl;
carboxymethyl-thio-p-chloro-phenoxy-isobutyric acid of the formula pCl—C$_6$H$_4$—O—C(CH$_3$)$_2$—CO—S—CH$_2$COOH and esters thereof;
N-acetyl methyl homocysteinate p-chlorophenoxy-2-isobutyrate, and the like.

The invention is illustrated by the following examples, without being confined to them. In the examples, the terms "soda" and "potash" mean "sodium hydroxide" and "potassium hydroxide," respectively.

EXAMPLE 1

Product 1: $ClC_6H_4O-C-(CH_3)_2-CO-S-CH_2-CH_2-CH(COOH)NH-CO-CH_3$.

1.75 g acetyl-homocysteine thiolactone was placed in a retort, followed by 25 ml normal soda and 20 ml water. This dissolved perfectly, and 2.33 g p-chlorophenoxyisobutyryl chloride was added, while the mixture was stirred, and without exceeding a temperature of 4° C. The mixture was left to react for 30 minutes at 5° C., and then allowed to return to room temperature. The product was purified by preparative chromatography on an alumina column. The aqueous fraction containing the product required was acidified to pH 3 with hydrochloric acid. This produced an oil, which crystallized after a few moments. It was recrystallized in the isopropanol-water mixture.

The final product took the form of white crystals, which had a melting point of 128° – 129° C. (Kofler unit). The gross formula was analyzed as follows:

| Content (%) | $C_{16}H_{20}ClNO_5S$ (molecular weight 373.86) | | | | |
|---|---|---|---|---|---|
| | C | H | Cl | N | S |
| Calculated: | 51.4 | 5.39 | 9.48 | 3.74 | 8.58 |
| Found: | 51.3 | 5.6 | 9.4 | 3.7 | 8.4 |

EXAMPLE 2

Product II: $pCl-C_6H_4-O-C(CH_3)_2-CO-S-CH_2-CH(COOH)-NH-CO-CH_3$

The same method was used as in Example 1, except that the acetyl-homocysteine thiolactone was replaced by acetyl cysteine thiolactone. The product was hard to isolate, and was simply extracted with ether, dried and evaporated. There was produced a viscous transparent mass; the gross formula was analyzed as follows:

| Content (%) | $C_{15}H_{18}ClNO_5S$ (molecular weight 359.83) | | | | |
|---|---|---|---|---|---|
| | C | H | Cl | N | S |
| Calculated: | 50.07 | 5.04 | 9.85 | 3.89 | 8.91 |
| Found: | 49.5 | 4.9 | 9.7 | 4 | 9.1 |

EXAMPLE 3

Product III: $pCl-C_6H_4-O-C(CH_3)_2-CO-S-CH_2-CH_2-OH$

The same method was used as in Example 1, except that the acetyl-homocysteine thiolactone was replaced by beta-mercaptoethanol. After reaction and purification, the product was extracted with ether, dried on sodium sulphate, and distilled in a vacuum after the ether had been evaporated.

The resulting product was an oil, which distilled at between 165° and 170° C at a pressure of 12 mm Hg, and was high yellow in color. The gross formula was analyzed as follows:

| Content (%) | $C_{12}H_{15}Cl\ O_3S$ (molecular weight 274.76) | | | |
|---|---|---|---|---|
| | C | H | Cl | S |
| Calculated: | 52.46 | 5.5 | 12.9 | 11.67 |
| Found: | 52.1 | 5.8 | 13 | 11.9 |

EXAMPLE 4

Product IV: $pCl-C_6H_4-O-C(CH_3)_2-CO-S-CH_2-CH_2-O-CO-C(CH_3)_2-O-C_6H_4pCl$ 20 ml pyridine dried on potash and 0.75 g mercaptoethanol were placed in a ground retort, surrounded by a cooler with a calcium chloride tube, and equipped with a stirring system. 4.66 g p-chlorophenoxy isobutyryl chloride was added slowly, without raising the temperature. The mixture was then heated by counterflow, maintained for an hour. The mixture was then cooled, poured into water, and purified by chromatography.

Fractions corresponding to the required product were mixed with 10 ml of 10% sodium bicarbonate (pH8). This produced an oily layer which crystallized after a few moments. It was dried and recrystallized in isopropanol.

The product took the form of white crystals with a melting point of 62°–3° C (Kofler unit). The gross formula was analyzed as follows:

| Content (%) | $C_{22}H_{24}Cl_2O_5S$ (molecular weight 471.40) | | | |
|---|---|---|---|---|
| | C | H | Cl | S |
| Calculated: | 56.06 | 5.13 | 15.04 | 6.8 |
| Found: | 55.7 | 5.4 | 14.8 | 7 |

EXAMPLE 5

Product V: $pCl-C_6H_4-O-C(CH_3)_2-CO-S-CH_2COOH$

The same method was used as in Example 1, except that the acetyl-homocysteine thiolactone was replaced by thioglycolic acid. The resulting product was obtained in the form of white crystals with a melting point of 47° C (Kofler unit). The gross formula was analyzed as follows:

| Content (%) | $C_{12}H_{13}Cl\ O_4S$ (molecular weight 288.74) | | | |
|---|---|---|---|---|
| | C | H | Cl | S |
| Calculated: | 49.92 | 4.54 | 12.28 | 11.1 |
| Found: | 50.3 | 4.3 | 12.5 | 11.2 |

EXAMPLE 6

Product VI: $Cl-C_6H_4-O-C(CH_3)_2-CO-S-CH_2-CH_2-CH(COOH_3)-NH-CO-CH_3$.

This product is an ester of the compound of formula (I).

2 g of product I obtained in Example 1 was placed in a retort, and dissolved in 20 ml methyl alcohol and saturated with anhydrous hydrochloric acid. The mixture was left still for 12 hours or so, and evaporated in a vacuum. The residue was recovered by means of 20 cc of 10% sodium bicarbonate. An oil separated out by decantation, and was found to crystallize quickly after rubbing. It was drained, dried and recrystallized in isopropanol, producing white crystals with a melting point of 92° C (Kofler unit). The formula was analyzed as follows:

$C_{17}H_{22}Cl\ NO_5S$ (molecular weight 387.89)

The product was characterized by the following composition (in proportions by weight):

|            | C     | H    | Cl   | N    | S    |
|------------|-------|------|------|------|------|
| Calculated:| 52.65 | 5.72 | 9.14 | 3.61 | 8.27 |
| Found:     | 53.1  | 5.8  | 9.25 | 3.7  | 8.4  |

Products I, II, III, IV, V and VI were tested pharmacologically for acute toxicity on mice, and for hypolipemient, hypocholesterolemient and hepatoprotective effects on rats and rabbits.

All six products had very low toxicity, with a $DL_{50}$ in all cases of more than 2,500 mg/kg for oral administration.

Compounds I, IV and V produced approximately twice as high a level of hypolipemient activity as clofibrate. Product I also had a very good hepatoprotective effect.

Pharmacological results for derivative I (Example 1) were as follows:

$DL_{50}$ per os in mice 4,500 mg/kg, while the figure for clofibrate is 2,000 mg/kg;

sub-chronic toxicity in rats after 45 days for a 200 mg/kg dose without affecting organs and without alteration in the weight curve;

comparative test on rats undergoing an atheromatous diet, followed by macroscopic and histological examination of control animals treated with 150 mg/kg clofibrate and 200 mg/kg of the tested product; there was a clear reduction in atheromatous patches in rats treated with product I, comparable with those treated with clofibrate;

increase in toxicity induced by carbon tetrachloride.

EXAMPLE 7

Product VII: $p-Cl-C_6H_4-O-C(CH_3)_2-CO-S-C_2H_5$

Ethyl mercaptan [2-(p-chlorophenoxy)-2-methyl propanoic] acid thiolester.

15.5 g ethyl mercaptan is dissolved in 300 ml 4% sodium hydroxide and cooled to 5° C.

65 g p-chlorophenoxy isobutyryl chloride (clofibryl chloride) are added to this mixture while stirring during a 15 minute period so as to maintain the temperature at 5°–10° C. The mixture is then allowed to react, while stirring, for an additional period of 30 minutes and the resulting oily product is extracted with ether, washed with water to pH 7 and dried over $Na_2SO_4$. The ether is evaporated under reduced pressure and the product distilled at 170°–175° C under 18 mm Hg, yielding an oily light yellow liquid.

| Content % | $C_{12}H_{15}ClO_2S$ (MW = 258.77) | | | |
|---|---|---|---|---|
|  | C | H | Cl | S |
| Calculated: | 55.69 | 5.84 | 13.70 | 12.39 |
| Found: | 50.0 | 5.84 | 14.20 | 12.20 |

EXAMPLE 8

Product VIII: $p-Cl-C_6H_4-O-C(CH_3)_2-CO-S-nC_4H_9$ n-butyl mercaptan [2-(p-chlorophenoxy)-2-methyl propanoic] acid thiolester.

The same procedure was followed as in Example 7, except for the use of n-butyl mercaptan instead of ethyl mercaptan. The product VIII when distilled at 189°–92° C under 15 mm Hg, yields an oily yellow liquid.

| Content % | $C_{14}H_{19}ClO_2S$ (MW = 286.82) | | | |
|---|---|---|---|---|
|  | C | H | Cl | S |
| Calculated: | 58.63 | 6.68 | 18.36 | 11.18 |
| Found: | 58.20 | 6.68 | 18.15 | 11.00 |

EXAMPLE 9

Product IX: $p-Cl-C_6H_4-O-C(CH_3)_2-CO-S-n(CH_2)_{11}-CH_3$ n-dodecyl mercaptan [2-(p-chlorophenoxy)-2-methyl propanoic] acid thiolester.

The same procedure was followed as in Example 7 except for the use of n-dodecyl mercaptan (lauryl mercaptan) instead of ethyl mercaptan.

The product IX cannot be distilled without decomposition. It is dissolved in ether and then washed and dried; the ether is evaporated under reduced pressure, and an oily light yellow product IX is obtained.

EXAMPLE 10

Product X: $p-I-C_6H_4-O-C(CH_3)_2-CO-S-CH_2-CH_2-CH(COOH)-NH-COCH_3$

2'-acetylamido 4'-thiobutanoic acid [2-(paraiodophenoxy)-2-methyl propanoic] acid thiolester.

1.75 g N-acetyl homocusteine thiolactone is dissolved in 50 ml 2% sodium hydroxide and 3.25 g p-iodophenoxy isobutyryl chloride is added while stirring, at about 15° C. The mixture is allowed to react for 30 minutes, until it becomes clear, and is then acidified to pH 2–3 by adding HCl; the product X precipitates and crystallizes after a few minutes. It is recrystallized in toluene. Product X is a white powderous solid, melting at 135° C (Kofler bank).

| Content % | $C_{16}H_{20}INO_5S$ (MW = 465.31) | | | |
|---|---|---|---|---|
|  | C | H | Cl | S |
| Calculated: | 41.30 | 4.33 | 3.01 | 6.89 |
| Found: | 41.20 | 4.33 | 3.20 | 7.10 |

EXAMPLE 11

Product XI: $p-Cl-C_6H_4-O-C(CH_3)_2-CO-S-C_6H_4-p-CH_3$ p-thiocresol [2-(parachlorophenoxy)-2-methyl propanoic] acid thiolester.

3.21 g p-thiocresol (4-mercapto toluene) are dissolved in 25 ml of 7% sodium hydroxide. The mixture is cooled to %° C; 2.50 g clofibryl chloride are added and the mixture is left to react, while stirring during 30 minutes at 5° to 10° C. The resulting crystals are collected, washed with water and recrystallized in ethanol.

Product XI is a white solid substance, melting at 68° C (Kofler bank).

| Content % | $C_{17}H_{17}ClO_2S$ (MW = 320.84) | | | |
|---|---|---|---|---|
|  | C | H | Cl | S |
| Calculated: | 63.64 | 5.34 | 11.05 | 9.99 |
| Found: | 62.90 | 5.34 | 11.70 | 10.20 |

EXAMPLE 12

Product XII: p—Cl—C$_6$H$_4$—O—C(CH$_3$)$_2$—CO—S—C$_6$H$_4$—p—NHCOCH$_3$ p-acetamido phenyl mercaptan [2-(parachlorophenoxy)-2-methyl propanoic] acid thiolester.

The same procedure was followed as in Example 11 except for the use of p-acetamido phenyl mercaptan and clofibryl chloride as starting reactants. Product XII is recrystallized in isopropanol and is a light yellow solid substance melting at 194° C (Kofler bank).

| | C$_{18}$H$_{18}$ClNO$_3$S (MW = 363.-) | | | | |
|---|---|---|---|---|---|
| Content % | C | H | Cl | N | S |
| Calculated: | 59.42 | 4.99 | 9.74 | 3.85 | 8.81 |
| Found: | 53.91 | 5.00 | 9.95 | 3.75 | 8.80 |

EXAMPLE 13

Product XIII:

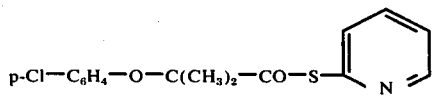

2-mercapto pyridine [2-(p-chlorophenoxy)-2-methyl propanoic] acid thiolester.

The same procedure was followed as in Example 11 except for the use of 2-mercapto pyridine and clofibryl chloride as starting reactants. Product XIII is recrystallized in cyclohexane. It is a yellow crystalline solid substance melting at 114° C on the Kofler bank.

| | C$_{15}$H$_{14}$ClNO$_2$S (MW = 307.-) | | | | |
|---|---|---|---|---|---|
| Content % | C | H | Cl | N | S |
| Calculated: | 58.53 | 4.58 | 11.52 | 4.55 | 10.42 |
| Found: | 59.10 | 4.62 | 11.75 | 4.40 | 10.20 |

EXAMPLE 14

Product XIV:

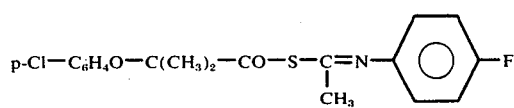

4'-fluoro phenyl (methyl) imino mercaptan [2-(parafluorophenoxy)-2-methyl propanoic] acid thiolester.

The same procedure was followed as in Example 11 except for the use of p-thiocresol para fluoro thioacetanilide which, under high (alkaline) pH conditions, leads to the mercaptan mesomeric form.

The product obtained is a pasty liquid which, after standing for 15 hours, crystallizes. After filtration and washing, the crystals are recrystallized in xylene; the white crystalline product thus obtained has a melting point of 152°–153° C (Kofler bank).

Naturally, the invention is in no way confined to the Examples given above which are given for purposes of illustration only. Many other variants are possible for someone skilled in the art, depending on applications involved, without any departure from the spirit of the invention.

What is claimed is:

1. A compound N-acetylhomocysteine-S-parachlorophenoxy-2-isobutyrate of the formula

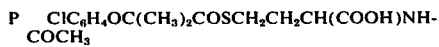

and esters thereof.

2. A compound N-acetylcysteine-S-parachlorophenoxy-2-isobutyrate of the formula

and esters thereof.

3. A compound 2'-acetylamido-4'-thiobutanoic acid [2-(paraiodophenoxy)-2-methyl propanoic acid] thiolester of the formula:

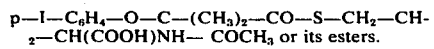

* * * * *